United States Patent
Hotta et al.

(10) Patent No.: US 6,617,414 B2
(45) Date of Patent: Sep. 9, 2003

(54) AROMATIC DIAMINE/AROMATIC DICARBOXYLATE AND PRODUCTION METHOD THEREOF

(75) Inventors: Kiyoshi Hotta, Shiga (JP); Fuyuhiko Kubota, Shiga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/736,337

(22) Filed: Dec. 15, 2000

(65) Prior Publication Data

US 2001/0014756 A1 Aug. 16, 2001

(30) Foreign Application Priority Data

Dec. 17, 1999 (JP) ............................ 11-359551

(51) Int. Cl.[7] ...................... C08G 63/00; C07C 63/313; C07C 63/36
(52) U.S. Cl. ...................... 528/184; 562/480; 562/490
(58) Field of Search ................ 528/184, 185; 562/480, 490; 564/306

(56) References Cited

U.S. PATENT DOCUMENTS 5,276,128 A   1/1994   Rosenberg et al. ......... 528/184

6,169,165 B1 * 1/2001 Kubota et al. .............. 528/486

FOREIGN PATENT DOCUMENTS

EP   0 805 173 A1   11/1997
EP   0 926 186 A1   6/1999

* cited by examiner

*Primary Examiner*—Richard L. Raymond
*Assistant Examiner*—Zachary C. Tucker
(74) *Attorney, Agent, or Firm*—Morrison & Foerster LLP

(57) ABSTRACT

The present invention provides aromatic diamine/aromatic dicarboxylate having the following formula (I)

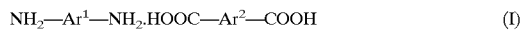

$$NH_2-Ar^1-NH_2 \cdot HOOC-Ar^2-COOH \qquad (I)$$

wherein each symbol is as defined in the specification, which is in the form of particles having a median diameter of 5–100 μm and whiteness of not less than 75. This salt has high polymerizability and preferably has superior storage stability. Therefore, it can be preferably used for the production of polybenzazole that can be formed into a fiber and a film having high strength, high elastic modulus and high heat resistance.

4 Claims, No Drawings

AROMATIC DIAMINE/AROMATIC DICARBOXYLATE AND PRODUCTION METHOD THEREOF

TECHNICAL FIELD OF THE INVENTION

The present invention relates to a monomer used for producing polybenzazole formable into a fiber and a film having high strength, high elastic modulus and high heat resistance. More particularly, the present invention relates to aromatic diamine/aromatic dicarboxylate having high polymerizability.

BACKGROUND OF THE INVENTION

Polybenzazole represented by polybenzoxazole and polybenzothiazole has been increasingly used for wider applications, such as reinforcing materials for rubber and plastic, industrial materials (e.g., heat resistant felt), and protective purposes (e.g., protective cloth for fire fighter and safety gloves), because it shows markedly high dynamic properties, heat resistance and flame resistance, among organic substances.

A typical production method of polybenzazole comprises subjecting aromatic diamine, such as 4,6-diamino-1,3-benzenediol, 2,5-diamino-1,4-benzenedithiol and the like, and aromatic dicarboxylic acid, such as terephthalic acid, naphthalenedicarboxylic acid, biphenyldicarboxylic acid and the like, to condensation polymerization in a solvent having a dehydrating effect, such as polyphosphoric acid and the like.

Aromatic diamine, which is a monomer of polybenzazole, is easily oxidized and handled in the form of an inorganic acid salt, which is more stable against oxidation and generally used as hydrochloride. When aromatic diamine hydrochloride is used for producing polybenzazole, however, a poisonous hydrogen chloride gas is generated in a large amount in an early stage of condensation polymerization. The generation of gas during reaction causes inflation of reaction volume and lowers the volume efficiency of a reactor, which is unpreferable from the aspect of productivity.

As a polybenzazole monomer free of gas generation, U.S. Pat. No. 5,276,128 discloses aromatic diamine/aromatic dicarboxylate. This is a monomer obtained by forming a salt from aromatic diamine and aromatic dicarboxylic acid in a 1:1 ratio, which does not contain a component that generates a gas, such as hydrogen chloride. When compared to the use of two kinds of monomers of aromatic diamine hydrochloride and aromatic dicarboxylic acid, moreover, weighing and charging is advantageously easier.

However, the aromatic diamine/aromatic dicarboxylate disclosed in the above-mentioned U.S. Pat. No. 5,276,128 does not have sufficient quality. The aromatic diamine/aromatic dicarboxylate has a chemical composition ratio of aromatic diamine and aromatic dicarboxylic acid of 1:1. If the polymerization degree is not controlled by the addition of a chain-end terminator and the like, polybenzazole having an extremely high polymerization degree should be obtained. However, the above-mentioned aromatic diamine/aromatic dicarboxylate is colored in pink or purple. This is considered to be attributable to partial decomposition of the constituent component, aromatic diamine.

As a result, the chemical composition of aromatic diamine and aromatic dicarboxylic acid is to be deviated, which prevents the polymerization degree of polybenzazole from increasing and reduces its viscosity. In an example of the above-mentioned USP, for instance, 4,6-diamino-1,3-benzenediol/terephthalate produces polybenzazole having an intrinsic viscosity of up to about 40 dl/g, and 2,5-diamino-1,4-benzenedithiol/terephtalate produces polybenzazole having an intrinsic viscosity of up to about 13 dl/g. In an example of EP 0805173A, a reaction is carried out at a low temperature for a long time to afford a polymer having a somewhat higher intrinsic viscosity of 48.5 dl/g than in the above-mentioned USP, from 4,6-diamino-1,3-benzenediol/terephtalate. However, the polymerization degree of the polymer is not sufficient.

When polybenzazole is produced from two kinds of monomers of aromatic diamine hydrochloride and aromatic dicarboxylic acid, a yellow polymer is generally obtained. When conventional aromatic diamine/aromatic dicarboxylate is used, only a polymer of a lower grade, which is colored in black to dark brown or dark purple to reddish purple, can be obtained.

In addition, conventional aromatic diamine/aromatic dicarboxylate shows markedly inferior stability against oxidation and heat as compared to aromatic diamine hydrochloride, which prevents long-term storage. Also, it frequently suffers from thermal degradation during production of polybenzazole. This has a consequence that the hue of the polymer becomes poor and the polymerization degree decreases.

SUMMARY OF THE INVENTION

It is therefore an object of the present invention to overcome low polymerizability, coloring of polymer and the like of conventional aromatic diamine/aromatic dicarboxylate, and to provide a monomer having a quality suitable for the production of polybenzazole, and a production method of aromatic diamine/aromatic dicarboxylate having such quality.

Such objects can be achieved by the present invention, wherein aromatic diamine/aromatic dicarboxylate in a particulate state and having a specific particle diameter and whiteness is polymerized to give polybenzazole having superior high polymerization degree and superior hue.

That is, the present invention provides aromatic diamine/aromatic dicarboxylate of the following formula (I)

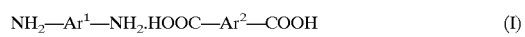

wherein $Ar^1$ is a group of the following formula (a) or (b)

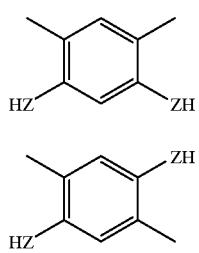

wherein each Z is independently an oxygen atom or a sulfur atom, and

Ar² is a group of any of the following formulas (c)–(f)

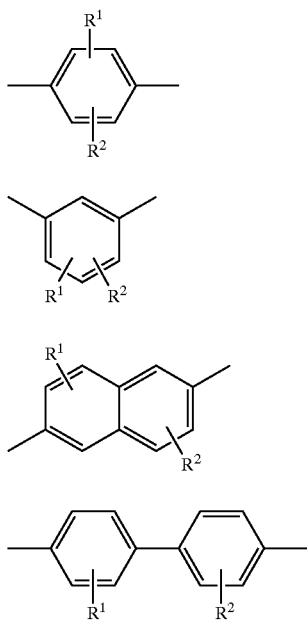

wherein R¹ and R² are each independently a hydrogen atom, a methyl group or a hydroxyl group,
which is in the form of particles having a median diameter of 5–100 μm and whiteness of not less than 75.

Preferably, the above-mentioned aromatic diamine/aromatic dicarboxylate has a water content of not more than 3000 ppm, and preferably contains tin(II) or iron(II) in a proportion of 0.1–5.0 mol %.

The present invention also provides a production method of the above-mentioned aromatic diamine/aromatic dicarboxylate, which comprises adding, for mixing, an aqueous solution of aromatic diamine hydrochloride of the following formula (II)

$$NH_2—Ar^1—NH_2 \cdot 2HCl \quad (II)$$

wherein Ar¹ is as defined above, to an aqueous solution of alkali metal aromatic dicarboxylate of the following formula (III)

$$MOOC—Ar^2—COOM \quad (III)$$

wherein Ar² is as defined above and M is an alkali metal, under the following conditions (1) and (2):

(1) 1.0–1.2 moles of the aromatic diamine hydrochloride is used per 1 mole of the alkali metal aromatic dicarboxylate, and
(2) a temperature during the addition is not less than 70° C. and not more than 100° C.

In addition, the present invention provides a production method of polybenzazole, which comprises using the above-mentioned aromatic diamine/aromatic dicarboxylate.

DETAILED DESCRIPTION OF THE INVENTION

The aromatic diamine/aromatic dicarboxylate of the present invention can be represented by the above-mentioned formula (I).

Examples of aromatic diamine in the aromatic diamine/aromatic dicarboxylate of the above-mentioned formula (I) include 4,6-diamino-1,3-benzenediol, 2,5-diamino-1,4-benzenediol, 4,6-diamino-1,3-benzenedithiol, 2,5-diamino-1,4-benzenedithiol and the like.

Examples of aromatic dicarboxylic acid in the aromatic diamine/aromatic dicarboxylate of the above-mentioned formula (I) include terephthalic acid, 2-methylterephthalic acid, monohydroxyterephthalic acid, dihydroxyterephthalic acid, phthalic acid, naphthalenedicarboxylic acid, biphenyldicarboxylic acid and the like.

In view of the easiness of obtaining a starting material, the aromatic diamine/aromatic dicarboxylate of the above-mentioned formula (I) is preferably that wherein aromatic diamine thereof is 4,6-diamino-1,3-benzenediol or 2,5-diamino-1,4-benzenedithiol, and aromatic dicarboxylic acid thereof is terephthalic acid or 2-methylterephthalic acid, with preference given to 4,6-diamino-1,3-benzenediol/terephtalate, 4,6-diamino-1,3-benzenediol/2-methylterephtalate and 2,5-diamino-1,4-benzenedithiol/terephtalate.

In the present invention, two or more kinds of the above-mentioned aromatic diamine/aromatic dicarboxylate may be used.

The aromatic diamine/aromatic dicarboxylate of the present invention is in the form of particles having a median diameter of 5–100 μm, more preferably 10–70 μm, particularly preferably 15–50 μm. When the median diameter of the salt is within the above-mentioned range, polybenzazole having a high polymerization degree can be produced. In general terms, when a polymer is polymerized in a solution, a monomer having a smaller particle diameter is considered to show greater solubility in the solvent, show faster progress of the reaction, and to be advantageous in producing a polymer having a high polymerization degree. In the case of aromatic diamine/aromatic dicarboxylate, however, a median diameter of less than 5 μm only affords polybenzazole having a smaller polymerization degree. This is postulated to be attributable to the heat stability of aromatic diamine/aromatic dicarboxylate, wherein a salt having a smaller particle diameter in fact tends to be subject to thermal decomposition. It is considered that, when a monomer has a median diameter of less than 5 μm, a polymer having a high polymerization degree cannot be obtained. This is attributable to the considerable influence of the thermal decomposition of the monomer. In contrast, when a monomer has a median diameter exceeding 100 μm, solubility in a solvent decreases, which in turn requires a longer time for polymerization reaction, during which the monomer tends to be influenced by the thermal decomposition. As used herein, by the median diameter is meant a value measured with a particle diameter distribution analyzer according to a laser diffraction/scattering method.

The aromatic diamine/aromatic dicarboxylate of the present invention has a whiteness of not less than 75, preferably not less than 80, more preferably not less than 85. When the salt has whiteness within this range, polybenzazole superior in hue can be obtained. When conventional aromatic diamine/aromatic dicarboxylate is used to produce polybenzazole, the originally yellow polymer turns to black-dark brown, red-reddish purple and the like. This aspect has been studied and it has been found that the use of aromatic diamine/aromatic dicarboxylate colored in pink, purple and the like results in polybenzazole having poor hue, wherein the degree of coloring of aromatic diamine/aromatic dicarboxylate influences the hue of the resulting polybenzazole.

When the coloring is noticeable, in other words, when the whiteness is less than 75, the polymer shows poor hue and a markedly lower polymerization degree. This is because coloring of aromatic diamine/aromatic dicarboxylate is caused by a degradation product of aromatic diamine, which is a constituent component of the salt. As used herein, by the whiteness is meant a value determined by the following formula based on Lab chromaticity measured with a commercially available colorimeter.

$$\text{Whiteness}=100-[(100-L)^2+(a^2+b^2)]^{1/2}$$

The aromatic diamine/aromatic dicarboxylate of the present invention can be produced by adding, for mixing, an aqueous solution of aromatic diamine hydrochloride of the following formula (II)

$$NH_2-Ar^1-NH_2 \cdot 2HCl \tag{II}$$

wherein $Ar^1$ is as defined above, to an aqueous solution of alkali metal aromatic dicarboxylate of the following formula (III)

$$MOOC-Ar^2-COOM \tag{III}$$

wherein $Ar^2$ is as defined above and M is an alkali metal, under the following conditions (1) and (2):

(1) 1.0–1.2 moles of the aromatic diamine hydrochloride is used per 1 mole of the alkali metal aromatic dicarboxylate, and (2) a temperature during the addition is not less than 70° C. and not more than 100° C.

Examples of aromatic diamine of the aromatic diamine hydrochloride of the above-mentioned formula (II) include those exemplified for the aromatic diamine of the aromatic diamine/aromatic dicarboxylate of the above-mentioned formula (I). Examples of aromatic dicarboxylate of the alkali metal aromatic dicarboxylate of the above-mentioned formula (III) include those exemplified for the aromatic dicarboxylic acid of the aromatic diamine/aromatic dicarboxylate of the above-mentioned formula (I).

The alkali metal expressed by M in the above-mentioned formula (III) may be, for example, sodium, potassium, lithium and the like, with preference given to sodium and potassium in view of high solubility in water.

The above-mentioned production method is explained in the following according to the order of steps involved.

First, aromatic diamine hydrochloride of the above-mentioned formula (II) is dissolved in water to give an aqueous solution of aromatic diamine hydrochloride. Water to be used for this purpose has been preferably deaerated with an inert gas such as nitrogen, helium and the like. To suppress the decomposition of aromatic diamine, a compound having a reducing effect may be added to the aqueous aromatic diamine hydrochloride solution. Examples of such compound include metal salts of tin(II), iron(II), copper(I) and the like, such as oxide, chloride, sulfide and the like, and phosphorus compound such as phosphonic acid and the like and sulfur compound such as sulfurous acid and the like, with preference given to tin(II) compound (particularly oxide and chloride).

Aromatic dicarboxylic acid is dissolved in an aqueous solution containing alkali metal hydroxide to give an aqueous solution of alkali metal aromatic dicarboxylate represented by the above-mentioned formula (III). Examples of alkali metal hydroxide include sodium hydroxide, potassium hydroxide and the like. This aqueous solution is preferably deaerated with an inert gas.

The above-mentioned aromatic diamine is preferably used in an equivalent amount with or in slightly excess of the above-mentioned aromatic dicarboxylic acid. That is, the amount of aromatic diamine hydrochloride to be used is preferably 1.0–1.2 moles, more preferably 1.0–1.1 moles, particularly preferably 1.0–1.05 moles, per 1 mole of alkali metal aromatic dicarboxylate. By setting the amounts of aromatic diamine hydrochloride and alkali metal aromatic dicarboxylate to be used to this level, aromatic diamine/aromatic dicarboxylate having the above-mentioned particle diameter and satisfactory hue can be obtained with good reproducibility. Conversely, when the amount of aromatic dicarboxylic acid is in excess, aromatic diamine/aromatic dicarboxylate, that affords a polymer having a high polymerization degree and superior hue, cannot be obtained easily.

The above-mentioned aqueous solution of aromatic diamine hydrochloride and aqueous solution of alkali metal aromatic dicarboxylate preferably have a higher concentration to achieve superior productivity. At a lower concentration, a salt having a greater median diameter is tend to be formed. To avoid this, it is set to at least not less than 0.2 mol/l, preferably not less than 0.3 mol/l, particularly preferably not less than 0.4 mol/l.

Then, the above-mentioned aqueous aromatic diamine hydrochloride solution and aqueous alkali metal aromatic dicarboxylate solution are mixed, thereby causing a salt exchange reaction, to obtain aromatic diamine/aromatic dicarboxylate as a white precipitate. Along therewith, a by-product of alkali metal halide, such as sodium chloride, potassium chloride and the like, is obtained.

To afford particles of the aromatic diamine/aromatic dicarboxylate having a median diameter of 5–100 μm, the temperature during mixing should be at least not less than 70° C., preferably not less than 80° C., more preferably not less than 90° C. When it is less than 70° C., the particle diameter becomes markedly small. In addition, the upper limit of the temperature during mixing needs to be maintained at not more than 100° C. When it exceeds 100° C., the thermal decomposition of aromatic diamine is promoted.

The aqueous aromatic diamine hydrochloride solution and the aqueous alkali metal aromatic dicarboxylate solution are preferably mixed by adding the aqueous aromatic diamine hydrochloride solution to the aqueous alkali metal aromatic dicarboxylate solution. When the aqueous alkali metal aromatic dicarboxylate solution is added to the aqueous aromatic diamine hydrochloride solution, the obtained aromatic diamine/aromatic dicarboxylate is frequently colored, and the whiteness thereof cannot be made to be not less than 75 easily. While the time for the addition varies depending on the scale of production, since a longer time shows the propensity toward easy coloring of the resultant product, it is preferably set for less than 2 hours.

The aromatic diamine/aromatic dicarboxylate obtained as mentioned above is filtered and washed with water to remove the salt produced alongside, such as sodium chloride, potassium chloride and the like. The filtering and water washing are preferably done in an inert gas atmosphere using, for example, nitrogen, helium and the like. Water to be used for the water washing is preferably deaerated in advance with an inert gas.

After filtration, the wet aromatic diamine/aromatic dicarboxylate is preferably dehydrated roughly by centrifugation, suction, pressurization and the like. Thereafter, it is preferably dried by reducing pressure under heating or by spraying a heated inert gas, such as nitrogen and the like.

When aromatic diamine/aromatic dicarboxylate having a high residual water content is heated, it tends to show discoloration by drying. Thus, the residual water content of this salt is preferably lowered to about not more than 50 wt % before heating.

The temperature during drying is preferably not more than 150° C., more preferably not more than 130° C., most preferably not more than 100° C., to avoid discoloration of the salt by drying. In addition, the temperature during drying does not need to be constant. The temperature may be low during the initial stage when the residual water content is high, and may be raised with the lapse of time.

For uniform drying and obliteration of lump (agglomerate of particles of the above-mentioned salt, having a large particle diameter), aromatic diamine/aromatic dicarboxylate is preferably placed under a flowing state by, for example, stirring, during processing. The drying time can be shortened by, for example, processing the wet aromatic diamine/ aromatic dicarboxylate in a water soluble organic solvent, such as methanol, ethanol, acetone and the like. However, it is not a desirable method because the organic solvent that remains in an ultramicro amount in the monomer after drying may adversely affect the production of polybenzazole.

The aromatic diamine/aromatic dicarboxylate obtained as above has high polymerizability and affords polybenzazole having fine hue.

The above-mentioned aromatic diamine/aromatic dicarboxylate has a water content of preferably not more than 3000 ppm, more preferably not more than 2000 ppm, particularly preferably not more than 1500 ppm. With this water content, it shows superior storage stability that enables maintaining of superior quality over several months.

For an improved storage stability, the above-mentioned aromatic diamine/aromatic dicarboxylate preferably contains an antioxidant. The antioxidant may be any as long as it does not interfere with the polymerization of polybenzazole. It is particularly preferably a tin(II) compound, such as tin(II) chloride, tin(II) oxide and the like, or an iron(II) compound, such as iron(II) chloride, iron(II) oxide and the like. The antioxidant is added in an amount appropriately set within the range of 0.1–5.0 mol % of aromatic diamine/ aromatic dicarboxylate. The antioxidant is appropriately added by, for example, dissolving it in an aromatic diamine solution or aromatic dicarboxylic acid solution and allowing incorporation into a salt during formation thereof, or by adding it while drying the salt.

The method for producing polybenzazole using the aromatic diamine/aromatic dicarboxylate of the present invention may be similar to the method disclosed in U.S. Pat. No. 4,533,693 and the like. To be specific, polyphosphoric acid is used as a dehydrating agent and polymerization solvent, and aromatic diamine/aromatic dicarboxylate is mixed with heating at 70–220° C. for condensation polymerization, thereby to obtain a condensed solution of polybenzazole, i.e., a dope. When condensation polymerization is carried out, the dehydrating effect of polyphosphoric acid may be enhanced by the addition of phosphoric acid anhydride.

The obtained polybenzazole dope is extruded from a spinning nozzle or die at 150–220° C., polyphosphoric acid is extracted by washing with water, and the resulting product is dried and formed into a fiber or a film having high strength, high elastic modulus and high heat resistance. On this occasion, a polymerization degree suitable for processing can be achieved, where necessary, by adding a chain-end terminator or by controlling the polymerization degree by the method disclosed in EP 0805173A.

The present invention is described in detail in the following by referring to a preferable embodiment. It is needless to say that the present invention is not limited to the embodiment.

Hydrochloride of aromatic diamine, such as 4,6-diamino-1,3-benzenediol and the like, is dissolved in water deaerated with nitrogen to give an aqueous aromatic diamine hydrochloride solution having a concentration of not less than 0.2 mol/l. A compound having a reducing effect may be added to this aqueous solution in a proportion of 0.1–5.0 mol % of the aromatic diamine hydrochloride. Separately, an aromatic dicarboxylic acid, such as terephthalic acid and the like, is dissolved in an aqueous solution containing alkali metal hydroxide, such as sodium hydroxide and the like, to give an aqueous alkali metal aromatic dicarboxylate solution having a concentration of not less than 0.2 mol/l, which solution is also deaerated with nitrogen. The aqueous aromatic diamine hydrochloride solution is added to the aqueous alkali metal aromatic dicarboxylate solution over several minutes to several dozen minutes to form a white precipitate of aromatic diamine/aromatic dicarboxylate. The amount of the aromatic diamine per 1 mole of aromatic dicarboxylic acid is 1.0–1.2 moles, and the reaction temperature is maintained at not less than 70° C. and not more than 100° C.

The reaction temperature is cooled to not more than 40° C. and aromatic diamine/aromatic dicarboxylate is filtered under a nitrogen stream. The wet aromatic diamine/aromatic dicarboxylate is dispersed in water deaerated with nitrogen and the dispersion is again subjected to filtration. This step of dispersing and filtering is repeated several times to remove alkali metal halide such as sodium chloride and the like.

The wet aromatic diamine/aromatic dicarboxylate is roughly dehydrated by centrifugation, suction, pressurization and the like to the water content of not more than 50 wt %. Thereafter, the dehydrated salt is transferred to an apparatus capable of drying in a flowing state, such as a rotary drier. The salt is dried by reducing the pressure under the conditions of not more than 10 Pa and not more than 150° C., to adjust the residual water content to not more than 3000 ppm. A compound having a reducing effect may be added in a proportion of about 0.1–5.0 mol % of the salt during drying.

The obtained aromatic diamine/aromatic dicarboxylate was evaluated for the quality by the measurement of the median diameter and whiteness, and further evaluated for polymerizability by a polymerization test.

The polymerizability is evaluated by adding polyphosphoric acid and phosphoric acid anhydride, the temperature thereof is stepwisely raised in a nitrogen stream from 70° C. to 220° C., and the mixture is heated and mixed to allow condensation polymerization to give polybenzazole, after which the obtained polybenzazole is dissolved in methanesulfonic acid, and the viscosity of the solution is measured.

The present invention is explained in detail by referring to examples. The present invention is not limited by these examples in any way. In the Examples, the median diameter, whiteness, water content, $Sn^{2+}$ content, and intrinsic viscosity of polymer were measured as follows.

1. Median diameter

Measured using a particle diameter distribution analyzer by laser diffraction/scattering method (manufactured by HORIBA, Ltd.), and chloroform as a dispersion solvent.

2. Whiteness

A sample (particles) was set in a sample holder of a colorimeter (manufactured by Nippon Denshoku Industries Co., Ltd.) and Lab chromaticity was measured, based on which whiteness was calculated from the following formula.

$$\text{Whiteness}=100-[(100-L)^2+(a^2+b^2)]^{1/2}$$

3. Water content

Measured using a Karl Fischer moisture titrator equipped with an evaporator (manufactured by Kyoto Electronics Manufacturing Co., Ltd.) at a gasification temperature of 120° C.

4. $Sn^{2+}$ Content

A sample was dispersed in 500 g/l aqueous citric acid solution and the content was measured using a polarography (manufactured by Metrohm Ltd.).

5. Intrinsic viscosity of polymer

Measured using Ostwald's viscometer at 25° C. in 0.1 M sodium methanesulfonate/distilled methanesulfonic acid.

EXAMPLE 1

4,6-Diamino-1,3-benzenediol dihydrochloride (350 g, 1.64 moles) was dissolved in water (1650 ml) deaerated with nitrogen. Terephthalic acid (265 g, 1.60 moles) was dissolved in 1M aqueous sodium hydroxide solution (3200 ml) and deaerated with nitrogen. The aqueous 4,6-diamino-1,3-benzenediol dihydrochloride solution was dropwise added to the aqueous disodium terephthalate solution over 10 minutes to form a white precipitate of 4,6-diamino-1,3-benzenediol/terephtalate. The reaction temperature was maintained at 90° C. The obtained salt was filtered, dispersed in water [3 L (liter)] aerated with nitrogen and the dispersion was again subjected to filtration. This step of dispersing and filtering was repeated three times. The salt washed with water was suctioned on a filter in a nitrogen atmosphere, and the moisture was removed to about 20 wt %. The dehydrated salt was dried by reducing the pressure under the conditions of 1 Pa and 80° C.

At 6 hr of drying, a part thereof was taken and used as a storage stability evaluation sample. The evaluation results are shown in Table 1. The sample had a median diameter of 37 μm, a residual water content of 4300 ppm and whiteness of 86.0. At 12 hr of drying, the finally-obtained salt had a median diameter of 38 μm, a residual water content of 870 ppm and whiteness of 85.6.

The finally-obtained salt was evaluated for polymerizability by the following trial polymerization.

The above-mentioned finally-obtained salt (13.1 g), 116% polyphosphoric acid (43.3 g), phosphoric acid anhydride (15.0 g) and tin(II) chloride dihydrate (0.1 g) were stirred for mixing at 80° C. The temperature was raised to 150° C. over 2 hr, and the mixture was reacted at 150° C. for 6 hr. The temperature was raised to 200° C. over 1 hr, and the mixture was reacted at 200° C. for 1 hr. The obtained poly (paraphenylenebenzobisoxazole) had a yellow hue and an intrinsic viscosity of 62 dl/g.

EXAMPLE 2

2,5-Diamino-1,4-benzenedithiol dihydrochloride (400 g, 1.63 moles) was dissolved in water (1500 ml) deaerated with nitrogen. Terephthalic acid (265 g, 1.54 moles) was dissolved in 1M aqueous sodium hydroxide solution (3200 ml) and deaerated with nitrogen. The subsequent steps followed Example 1. The obtained 2,5-diamino-1,4-benzenedithiol/terephtalate had a median diameter of 25 μm, a residual water content of 930 ppm and whiteness of 80.3.

The following trial polymerization was conducted.

The above-mentioned salt (14.5 g), 116% polyphosphoric acid (43.3 g), phosphoric acid anhydride (15.0 g), and tin(II) chloride dihydrate (0.1 g) were stirred for mixing at 80° C. The mixture was reacted at 150° C. for 10 hr and at 200° C. for 2 hr. The obtained poly(paraphenylenebenzobisthiazole) had a yellow hue and an intrinsic viscosity of 42 dl/g.

EXAMPLE 3

4,6-Diamino-1,3-benzenediol dihydrochloride (350 g, 1.64 moles) was dissolved in water (1650 ml) deaerated with nitrogen. 2-Methylterephthalic acid (289 g, 1.60 moles) was dissolved in aqueous sodium hydroxide solution (128 g/water 3800 ml) and deaerated with nitrogen. The subsequent steps followed Example 1. The obtained 4,6-diamino-1,3-benzenediol/2-methylterephtalate had a median diameter of 25 μm, a residual water content of 1050 ppm and whiteness of 87.7.

The following trial polymerization was conducted.

The above-mentioned salt (13.7 g), 116% polyphosphoric acid (43.3 g), phosphoric acid anhydride (15.0 g), and tin(II) chloride dihydrate (0.1 g) were stirred for mixing at 80° C. The mixture was reacted at 150° C. for 10 hr and at 200° C. for 2 hr. The obtained poly(2-methylparaphenylenebenzobisthiazole) had a yellow hue and an intrinsic viscosity of 55 dl/g.

EXAMPLE 4

In the same manner as in Example 1 except that tin(II) chloride dihydrate (4.4 g, 0.02 mole) was added to an aqueous 4,6-diamino-1,3-benzenediol dihydrochloride solution, the steps were performed. At 6 hr of drying, a part thereof was taken and used as a sample. The sample had a median diameter of 45 μm, a residual water content of 4880 ppm, whiteness of 88.1 and an $Sn^{2+}$ content of 0.58 mol %.

At 12 hr of drying, the finally-obtained 4,6-diamino-1,3-benzenediol/terephtalate had a median diameter of 47 μm, a residual water content of 950 ppm, whiteness of 89.3 and an $Sn^{2+}$ content of 0.55 mol %.

In the same manner as in Example 1 except that tin(II) chloride dihydrate was not added, the finally-obtained salt was subjected to trial polymerization. The obtained poly (paraphenylenebenzobisoxazole) had a yellow hue and an intrinsic viscosity of 64 dl/g.

COMPARATIVE EXAMPLE 1

In the same manner as in Example 1 except that the reaction temperature was set to room temperature, the steps were followed. The obtained 4,6-diamino-1,3-benzenediol/terephthalate had a median diameter of 2 μm, a residual water content of 950 ppm and whiteness of 82.3. In the same manner as in Example 1, a sample was taken at 6 hr of drying and subjected to the storage stability evaluation. The evaluation results are shown in Table 1.

The obtained salt was subjected to trial polymerization in the same manner as in Example 1. The obtained poly (paraphenylenebenzobisoxazole) had a dark brown hue and an intrinsic viscosity of 38 dl/g.

COMPARATIVE EXAMPLE 2

The addition method in Example 1 was reversed. That is, an aqueous disodium terephthalate solution was dropwise added to an aqueous 4,6-diamino-1,3-benzenediol dihydrochloride solution. Other conditions were the same. The obtained 4,6-diamino-1,3-benzenediol/terephthalate had a median diameter of 32 μm, a residual water content of 810 ppm and whiteness of 68.7.

The obtained salt was subjected to trial polymerization in the same manner as in Example 1. The obtained poly (paraphenylenebenzobisoxazole) had a reddish purple hue and an intrinsic viscosity of 24 dl/g.

COMPARATIVE EXAMPLE 3

In the same manner as in Example 1 except that the drop addition was performed over 3 hr, the steps were followed. The obtained 4,6-diamino-1,3-benzenediol/terephthalate had a median diameter of 48 μm, a residual water content of 680 ppm and whiteness of 58.8.

The obtained salt was subjected to trial polymerization in the same manner as in Example 1. The obtained poly (paraphenylenebenzobisoxazole) had a dark purple hue and an intrinsic viscosity of 15 dl/g.

COMPARATIVE EXAMPLE 4

4,6-Diamino-1,3-benzenediol dihydrochloride (21.4 g, 0.10 mole) was dissolved in water (100 ml) deaerated with nitrogen. Terephthalic acid (16.1 g, 0.10 mol) was dissolved in aqueous sodium hydroxide solution (8 g/water 1000 ml) and deaerated with nitrogen. The subsequent steps followed Example 1. The obtained 4,6-diamino-1,3-benzenediol/terephtalate had a median diameter of 116 μm, a residual water content of 520 ppm and whiteness of 78.7.

The obtained salt was subjected to trial polymerization in the same manner as in Example 1. The obtained poly (paraphenylenebenzobisoxazole) had a reddish purple hue and an intrinsic viscosity of 21 dl/g.

EXPERIMENTAL EXAMPLE 1

4,6-Diamino-1,3-benzenediol/terephtalate obtained in Example 1 and Comparative Example 1, which had different median diameters, were evaluated for the thermal decomposability as follows.

Each sample was heated at 200° C. in a nitrogen atmosphere. Each sample was taken every 2 hr thereafter, and evaluated for the whiteness. The results are shown in Table 1.

TABLE 1

| | Median diameter | Whiteness Nitrogen atmosphere, 200° C., heating time | | |
|---|---|---|---|---|
| | | 0 hr | 2 hr | 4 hr |
| Example 1 | 38 μm | 85.6 | 79.0 | 70.7 |
| Comparative Example 1 | 2 μm | 82.3 | 68.5 | 56.1 |

As shown in Table 1, the salt of Comparative Example 1 was colored faster than was the salt of Example 1, and is considered to be susceptible to thermal decomposition.

The aromatic diamine/aromatic dicarboxylate of the present invention shows extremely high polymerizability, affords polybenzazole having superior hue and is preferably superior in storage stability. Therefore, it has higher quality than the conventional salts. Moreover, the production method of aromatic diamine/aromatic dicarboxylate of the present invention is a superior method that enables easy production of aromatic diamine/aromatic dicarboxylate having the above-mentioned high quality.

Accordingly, the aromatic diamine/aromatic dicarboxylate and the production method thereof of the present invention are considered to contribute greatly to the field of formed and processed articles of polybenzazole represented by polybenzoxazole and polybenzothiazole.

This application is based on application No. 359551/1999 filed in Japan, the contents of which are incorporated hereinto by reference.

What is claimed is:

1. An aromatic diamine/aromatic dicarboxylate composition comprising an aromatic diamine/aromatic dicarboxylate of the following formula (I)

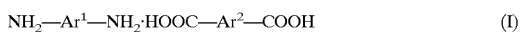

wherein $Ar^1$ is a group of the following formula (a) or (b)

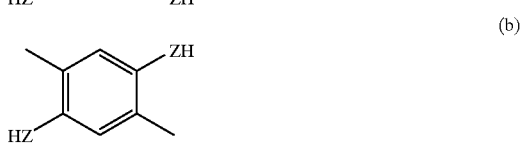

wherein each z is independently an oxygen atom or a sulfur atom, and $Ar^2$ is selected from the group consisting of the following formulas (c)–(f)

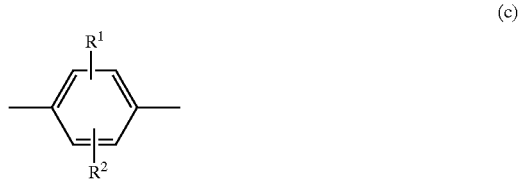

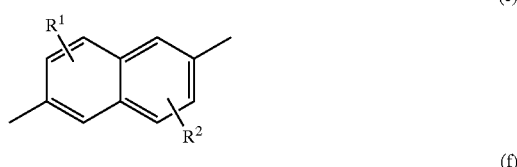

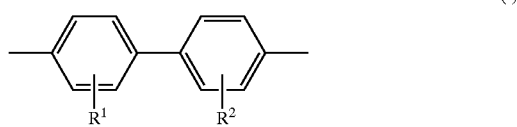

wherein $R^1$ and $R^2$ are each independently a hydrogen atom, a methyl group or a hydroxyl group, which is in the form of particles having a median diameter of 5–100 μm and whiteness of not less than 75; and further comprising tin (II) or iron (II) in a proportion of 0.1 to 5.0 mol %.

2. The aromatic diamine/aromatic dicarboxylate composition of claim 1, which has a water content of not more than 3000 ppm.

3. A production method of aromatic diamine/aromatic dicarboxylate composition of claim 1, which comprises adding, for mixing, an aqueous solution of aromatic diamine hydrochloride of the following formula (II)

$$NH_2-Ar^1-NH_2 \cdot 2HCl \quad (II)$$

wherein $Ar^1$ is as defined in claim 1, to an aqueous solution of alkali metal aromatic dicarboxylate of the following formula (III)

$$MOOC-Ar^2-COOM \quad (III)$$

wherein $Ar^2$ is as defined in claim 1 and M is an alkali metal, under the following conditions (1) and (2):

(1) 1.0–1.2 moles of the aromatic diamine hydrochloride is used per 1 mole of the alkali metal aromatic dicarboxylate, and (2) a temperature during the addition is not less than 70° C. and not more than 100° C.

4. A production method of polybenzazole, which comprises polymerizing the composition of claim 1.

* * * * *